United States Patent [19]

Florin et al.

[11] Patent Number: 5,138,793
[45] Date of Patent: Aug. 18, 1992

[54] PROCESS FOR THE PRESERVATION OF PLANT EMBRYOS

[75] Inventors: Bruno Florin; Vincent Petiard, both of Tours, France

[73] Assignee: Nestec S.A., Vevey, Switzerland

[21] Appl. No.: 543,475

[22] Filed: Jun. 25, 1990

[30] Foreign Application Priority Data

Jul. 18, 1989 [FR] France .................................. 89 09639

[51] Int. Cl.⁵ .......................... A01C 1/06; C12N 5/02; C12N 5/04
[52] U.S. Cl. .................. 47/57.6; 435/240.4; 435/240.49; 47/58
[58] Field of Search .................. 435/240.4, 240.49; 47/57.6

[56] References Cited

U.S. PATENT DOCUMENTS 4,615,141 10/1986 Janick et al. .................. 47/57.6

OTHER PUBLICATIONS

Augereau et al., Long Term Storage of Callus Cultures at Low Plant Cell Reports vol. 5, pp. 372-376 1986.
Caplin; Mineral Oil Overlay for Conservation of Plant Tissue Cultures Am. Journal of Botany, vol. 46, pp. 324-329 1959.

Primary Examiner—John Doll
Assistant Examiner—George C. Elliott
Attorney, Agent, or Firm—Vogt & O'Donnell

[57] ABSTRACT

Plant embryos are preserved by coating a plant embryo with oil in an amount sufficient for causing hypoxia and then cooling and storing the coated embryo at a temperature above the cold sensitivity threshold of the embryo.

19 Claims, No Drawings

PROCESS FOR THE PRESERVATION OF PLANT EMBRYOS

BACKGROUND OF THE INVENTION

This invention relates to a process for the preservation of plant embryos.

Numerous species of plants may be preserved and stored in the form of cell suspensions, calluses or even meristems.

The storage of plant embryos is justified in many cases, for example for regulating the production of plantlets where it is seasonal or for maintaining a clonal line. The preservation of plant embryos can have various advantages, including for example the possibility of temporarily stopping the development of the embryos, the time required for their transport to the seed bed or for their storage and the possibility of producing artificial seeds.

Somatic embryos have certain advantages for the multiplication of plants. They emanate in principle from a single cell and give genetically identical plants. From the beginning of their formation, somatic embryos have a bipolar structure: they have the two, meristems i.e., stem and root necessary to produce a plant. Accordingly, somatic embryogenesis appears an interesting alternative for the propagation of plants. It could be used for the rapid multiplication of species that are expensive to produce or of high-performance individuals emanating from in vitro cultures or of transformed plants that are difficult to reproduce sexually for example.

There are various known processes for storing undifferentiated tissues at low temperatures and/or under hypoxia. Generally speaking, the tissues are kept on a semi-solid medium or are stored at a temperature below 0° C.

One known process comprises storing grape calluses at a temperature of 10° C. or 15° C. To increase their storage life, a layer of silicone oil may be added to the calluses, although they remain on their nutrient substrate. Another process which may be applied to yeasts or cells comprises forming an aqueous emulsion of the cells using an oil medium and cooling the whole to a temperature of the order of $-20°$ C.$-30°$ C. so that the water remains supercooled. The oil thus acts as a cryoprotective agent, for the cells or yeasts.

SUMMARY OF THE INVENTION

The object of the present invention is to provide a process for the preservation of plant embryos by which the growth of the embryos isolated from their culture medium may be slowed down significantly for a predetermined time and then resumed without the appearance of secondary embryogenesis.

To this end, the process according to the present invention is characterized in that the embryos are kept under hypoxia by coating with a layer of oil, after which the embryos are cooled and stored at a temperature slightly above the cold sensitivity threshold of the embryos in question.

It has surprisingly been found that, by keeping the embryos under hypoxia in oil at a low temperature, their growth may be partly and durably inhibited without any effect on their viability and germinating power while, at the same time, the integrity of the structure of the embryo during its subsequent growth is maintained without the appearance of any other form of morphogenesis, such as callogenesis or secondary embryogenesis, either in light or in darkness. In other words, the process according to the invention for the preservation of plant embryos on the one hand enables the embryos to survive in their morphological integrity and, on the other hand, enables them effectively to retain their capacity to develop a plantlet.

Accordingly, another advantage of this process is that it enables embryos to be stored for relatively long periods. Another advantage of the process is that it enables embryos to be stored at readily accessible temperatures, for example, in a refrigerator, without having to use expensive equipment. Another advantage of the invention is that it provides a process which can be carried out quickly and easily both in darkness and in light.

DETAILED DESCRIPTION OF THE INVENTION

The embryos used in the present invention may be of any origin and any species, such as carrots or coffee trees, for example.

The embryos may be somatic embryos or zygotic embryos.

The somatic embryos may be obtained from undifferentiated cell suspensions. In this case, seeds of a hybrid parent for example may be aseptically germinated. The hypocotyls may be cut and then placed on a culture medium containing growth hormones. The calluses obtained may then be dissociated in a liquid culture medium. This gives an undifferentiated cell suspension of which the cells, after several subcultures, may be transferred to a culture medium. After about ten days, the cell suspension may be filtered so that only cell aggregates of the required size are retained. These aggregates may be cultured for a few days on a hormone-free culture medium to induce formation of the embryos.

The zygotic embryos may be obtained by sampling by dissection of the seeds at the mature or slightly immature stage.

The somatic and zygotic embryos obtained may be classified according to their stage of development. Preferred embryos are in the initial stages of their development when they are between 150 and 1000 μm in size. These sizes correspond to the heart or torpedo stages of their development.

The embryos obtained may then be washed, for example with a liquid culture medium free from growth hormones of the type typically encountered in embryo culture, such as a Murashige and Skoog medium containing 5 g/l sucrose. The washed embryos may then be transferred to culture plates and dried by withdrawal of the residual culture medium, for example by means of a pipette.

The embryos ar then kept under hypoxia by coating with a layer of oil. The oil is selected for its ability to cause hypoxia, i.e., to transfer little, if any, external oxygen to the embryo. The oil acts as a preservative and provides the embryo with the minimum quantity of oxygen required for its survival. The oil used for maintaining hypoxia may be a mineral oil, an oil of vegetable origin, a synthetic oil or any other oil capable of maintaining hypoxia without being toxic towards the embryos. The oil used is preferably a liquid paraffin oil. The oil may be degassed and/or sterilized beforehand, for example by autoclaving for 20 minutes at 115° C.

The quantity of oil added should be sufficient to coat the embryos completely. The oil is preferably added in a quantity of 0.02 to 0.5 ml per embryo.

The embryos are then cooled to a temperature just above the cold sensitivity threshold of the embryos in question. The cold sensitivity threshold is understood to be the temperature below which the embryos are no longer viable. The temperature to which the embryos are cooled and then stored may be a few degrees, preferably 1° to 10° C., above the cold sensitivity threshold.

The storage temperature may be, for example, between 2° and 8° C. and preferably between 3° and 5° C. for embryos of species that are only slightly sensitive to cold, such as carrots. It may be between 12° and 20° C. and preferably between 15° and 17° C. for embryos of species that are more sensitive to cold, for example species of tropical origin, such as coffee trees for example.

The embryos may be cooled, for example, by transferring the culture plates containing the embryos to a refrigerator or air-conditioned chamber. The cooling rate may be fairly rapid, for example of the order of 1° to 3° C. per minute.

The embryos under hypoxia in oil may be stored in weak light (of the order of 200 lux) or in darkness.

The process according to the invention ensures the survival of embryos stored in darkness. This can have a practical advantage in cases where artificial seeds are subsequently produced by encapsulation of the embryo. This is because it appears probable that no residual lighting reaches the embryo inside the capsule. The embryos may be stored under these conditions for relatively long periods, i.e., for approximately two to four months.

After storage, the embryos may be removed from the refrigerator and reheated to ambient temperature. When they have reached a temperature of the order of 20° C., they may be washed with a typical liquid culture medium to eliminate any trace of oil.

They may then be placed in or on a typical culture medium, such as a Murashige and Skoog medium, where they resume normal growth comparable with that of embryos which have not been stored.

For distribution among users with a view to conventional sowing in a seed bed or in a field, the embryos may be encapsulated in more resistant materials which afford them protection comparable with that of natural seeds. In this case, the oil-coated embryos may be encapsulated in natural or artificial polymers, for example a sodium alginate gel. These capsules afford the embryo mechanical and hygienic protection and provide for feeding of the plantlet during its germination.

The capsules may be subsequently coated with an additional film, for example of a water-soluble resin, which partly protects them against breaking and drying out. It is possible in this way to obtain an artificial seed which keeps for longer periods, namely for the time required for their practical application.

EXAMPLES

The present invention is illustrated in more detail in the following Examples. These Examples are preceded by an example of the conventional preparation of somatic embryos, by the description of a viability test and by Table 1 which gives the composition of the preferred culture medium used.

Example of the Preparation of Somatic Embryos

An undifferentiated cell culture of carrot cells (*Daucus carota* L.) is subcultured every 12 days (1 gram biomass to 100 ml medium) in a Murashige and Skoog liquid culture medium containing 20 g/l sucrose and 0.1 mg/l 2,4-dichlorophenoxyacetic acid.

All handling is carried out under aseptic conditions beneath a laminar flow hood. The suspension is placed on a stirrer making an eccentric gyratory movement of 100 r.p.m. and is cultured at 23° C. under 200 lux lighting with a photoperiod of 16 hours.

After culture for 8 to 10 days, the cell suspension is filtered so that only cell aggregates between 50 and 200 $\mu$m in size are retained. These small aggregates represent a proembryonic stage of the embryos which will continue their development to the heart, torpedo and plantlet stages. The aggregates are washed and placed in a Murashige and Skoog medium containing no 2,4-dichlorophenoxyacetic acid in a quantity of approximately $1.5 \times 10^3$ aggregates per ml medium.

After culture for 10 days, embryos have formed. The suspension is filtered so that only embryos between 150 and 1000 $\mu$m in size are retained.

Viability Test

A quick and simple viability test has been developed to evaluate the viability rate of the embryos after freezing.

Among the various criteria which may be used to evaluate the viability rate of the embryos,
the increase in the size of the embryos and
the appearance of a chlorophyllian coloration are particularly appropriate.

These criteria may be evaluated in various ways, for example by visual counting or by biochemical tests (coloration test for example).

Under the principle of this test, the embryos are placed in a typical liquid or semi-solid culture medium. After culture for 10 days, the number of embryos which have increased in size and show signs of chlorophyllian coloration is recorded. The ratio between this number and the total number of embryos present enables the viability rate of the embryos to be determined.

The embryos may then be kept on the same liquid medium or may be placed on a solid culture medium having the same composition as the preceding liquid medium so that they may continue their development to the plantlet stage. After culture for 10 days on this medium, the conversion level is determined as the ratio between the number of embryos which have developed to the plantlet stage and the total number of embryos.

TABLE 1

| Composition of the Murashige and Skoog medium (pH 5.8-6) | |
|---|---|
| Macroelements | mg l$^{-1}$ |
| NH$_4$NO$_3$ | 1650 |
| CaCl$_2$.2H$_2$O | 440 |
| MgSO$_4$.7H$_2$O | 370 |
| KNO$_3$ | 1900 |
| KH$_2$PO$_4$ | 170 |
| Microelements | |
| CoCl$_2$ | 0.025 |
| CuSO$_4$.5H$_2$O | 0.025 |
| FeSO$_4$.7H$_2$O | 27.8 |
| Na$_2$-EDTA | 37.3 |
| MnSO$_4$.4H$_2$O | 22.3 |
| KI | 0.83 |
| Na$_2$MoO$_4$ | 0.25 |
| ZnSO$_4$.7H$_2$O | 10.6 |

TABLE 1-continued

| Composition of the Murashige and Skoog medium (pH 5.8-6) | |
|---|---|
| $H_3BO_3$ | 6.2 |
| Other elements | |
| Nicotinic acid | 5 |
| Thiamine (vit. $B_1$) | 2 |
| Adenine | 2 |
| Sucrose | 5,000 |

EXAMPLE 1

Somatic carrot embryos at the torpedo stage (average size 670 μm) obtained as described above are washed with a liquid Murashige and Skoog culture medium. The embryos are then placed on culture plates consisting of 6 cups in a quantity of 20/30 embryos per cup and are freed from traces of residual culture medium by withdrawal of the liquid with a pipette.

Two groups (A) and (B) of embryos are coated with a layer of liquid paraffin oil sterilized beforehand by autoclaving for 20 minutes at 115° C. 1 ml oil is then added for 5 to 8 embryos. Two control groups (C) and (D) of embryos are coated with the liquid culture medium.

The culture plates are then covered with their cover and hermetically sealed. A first group (A) of embryos under hypoxia in oil is placed in a chamber cooled to 4° C. For comparison, a second group (B) of embryos under hypoxia in oil is kept at 23° C. A first control group (C) of embryos which are not under hypoxia is stored at 4° C. while a second control group (D) is stored at 23° C.

The various groups are stored under light of 200 lux.

After a certain storage time, the embryos are reheated to ambient temperature and a liquid culture medium is injected beneath the layer of oil surrounding the embryos under hypoxia in order to transfer as many embryos as possible to the culture medium.

After elimination of the layer of oil, the embyros are washed in several successive baths of culture medium to eliminate every trace of residual oil.

The development of the size of the embryos during the storage period is observed by measurement of their size with a binocular magnifying glass equipped with a measuring eyepiece.

The following results are obtained: Size of the embryos (μm)

| | Storage time (days) | | | | | |
|---|---|---|---|---|---|---|
| | 0 | 14 | 35 | 49 | 63 | 105 |
| Group A (4° C.) | 670 | 674 | 732 | 762 | 854 | 1327 |
| Group B (23° C.) | 670 | 2863 | 2896 | — | — | — |
| Control (4° C.) | 670 | 688 | 1104 | 1292 | 1536 | 3310 |
| Control (23° C.) | 670 | 10500 | — | — | — | — |

It can be seen that the embryos stored at 23° C. grow fairly rapidly whether or not they are under hypoxia. After 14 days, they have more than tripled in size whereas the embryos stored at 4° C. have hardly grown. After 105 days, the embryos stored at 4° C. under hypoxia in oil are still relatively small in size whereas the control embryos stored at 4° C. in culture medium have continued to grow.

At the same time, it can be seen that storage under hypoxia in oil at 4° C. influences the viability of the embryos.

To this end, the embryos freed from the layer of oil and reheated to ambient temperature are cultured in the Murashige and Skoog liquid culture medium.

The viability of the embryos is evaluated by the resumption or continuation of their growth in liquid medium.

After culture for 10 days, the viability level of the embryos is determined.

The following results are obtained: Viability level: (expressed in % of growth resumption)

| | Storage time (days) | | | | | |
|---|---|---|---|---|---|---|
| | 0 | 14 | 35 | 49 | 63 | 105 |
| Group A (4° C.) | 97 | 94 | 97 | 92 | 90 | 65 |
| Group B (23° C.) | 97 | 96 | 18 | 0 | — | — |
| Control (4° C.) | 97 | 92 | 92 | 91 | 87 | 83 |
| Control (23° C.) | 97 | 90 | — | — | — | — |

The embryos stored under hypoxia in oil at 4° C. have a correct viability level after storage for 105 days whereas the embryos stored under hypoxia at 23° C. are no longer viable after a storage time of 35 days.

The control embryos stored at 4° C. also show good viability after 105 days, but are then too large in size (approx. 3300 μm) to allow possible storage by encapsulation in a polymer.

After culture for 20 days in the liquid medium, the number of embryos which have developed a normal plantlet is determined.

The following results are obtained: Conversion level (expressed in % of plantlets grown)

| | Storage time (days) | | | |
|---|---|---|---|---|
| | 0 | 35 | 63 | 105 |
| Group A (4° C.) | 97 | 99 | 80 | 36 |
| Control (4° C.) | 97 | 86 | 23 | 0 |

The embryos stored at 4° C. under hypoxia in oil continue to grow without the appearance of adventitious proliferation in exactly the same way as the control embryos.

The partial inhibition of the growth of the somatic embryos by keeping them under hypoxia in oil at 4° C. does not affect the viability of the embryos or their ability to resume growth.

EXAMPLE 2

Somatic carrot embryos (average size 460 μm) are stored at 4° C. by the method described in Example 1. The embryos are partly stored in darkness and, for comparison, partly in light of 200 lux.

The development of the size of the embryos during the storage period is observed.

The following results are obtained: Size of the embryos (μm)

| | Storage time (days) | | | | | | |
|---|---|---|---|---|---|---|---|
| | 0 | 18 | 29 | 46 | 61 | 81 | 95 |
| Hypoxia in oil darkness | 460 | 596 | 601 | 701 | 625 | 545 | 554 |
| Hypoxia in oil 200 lux | 460 | 610 | 603 | 659 | 547 | 651 | 548 |
| Control, darkness | 460 | 999 | 1325 | 2811 | 3644 | 7454 | 11670 |
| Control, 200 lux | 460 | 1120 | 1508 | 2493 | 4634 | 7602 | 9941 |

It can be seen that the embryos kept under hypoxia in oil have hardly developed in size whether stored in light or in darkness.

Exposure to light during storage of the embryo does not appear to affect its viability. The absence of light has no effect on the degree of inhibition induced by the combination of hypoxia in oil and a low temperature.

EXAMPLE 3

Somatic embryos of the coffee tree, Coffea arabica, at the advanced torpedo stage (average size 1590 μm) are washed and placed on culture plates by the method described in Example 1.

Three groups (A), (B) and (C) of embryos are coated with a layer of sterilized liquid paraffin oil in a quantity of approximately 1 ml oil for 5 to 8 embryos. Three control groups of embryos are coated with a Murashige and Skoog liquid medium.

One group (A) of embryos under hypoxia in oil is stored at 4° C., a second group (B) at 10° C. and a third group (C) at 15° C. A first control group is stored at 4° C., a second at 10° C. and a third at 15° C.

The groups are kept in darkness for one month and are then returned to ambient temperature. The embryos are washed by the method described in Example 1 and are then cultured on a Murashige and Skoog semi-solid medium.

After culture for 10 days, the viability level of the embryos is determined.

The following results are obtained: Viability level (% growth resumption)

| | | |
|---|---|---|
| Group A (4° C.) | 0 | |
| Group B (10° C.) | 0 | comparison |
| Group C (15° C.) | 80 | |
| Control (4° C.) | 0 | |
| Control (10° C.) | 0 | comparison |
| Control (15° C.) | 84 | |

It can be seen that the embryos stored at 4° C. or 10° C. turn brown and die whether they are under hypoxia in oil or in a liquid culture medium.

The coffee tree embryos keep well at a temperature of 15° C.

It is thus important to take into account the cold sensitivity threshold of the species in question for the purpose of determining the minimum storage temperature.

EXAMPLE 4

Somatic coffee tree embryos at the advanced torpedo stage (average size 1590 μm) are stored at 15° C. under hypoxia in oil by the method described in Example 1.

After storage for 1 or 2 months, the embryos are reheated to ambient temperature and washed.

The development of the size of the embryos during the storage period is observed.

The following results are obtained: Size of the embryos (μm)

| | Storage time | | |
|---|---|---|---|
| | 0 | 1 month | 2 months |
| Embryos under hypoxia in oil | 1590 | 1680 | 1710 |
| Control embryos | 1590 | 2780 | 3590 |

It can be seen that the embryos under hypoxia in oil grow much more slowly than the control embryos.

The viability of the embryos is determined after culture for 10 days on semi-solid medium. It is 70% for the embryos stored for 2 months under hypoxia in oil and 84% for the control embryos stored for 2 months in the liquid culture medium. Coating of the embryos with a layer of oil thus enables their growth to be effectively inhibited without seriously affecting their viability.

EXAMPLE 5

Somatic coffee tree embryos at the advanced heart stage (average size 1100 μm) or at the torpedo stage (average size 1320 μm) are stored in darkness at 15° C. for one month either under hypoxia in paraffin oil or in a liquid culture medium by the method described in Example 1.

After storage, the embryos are reheated to ambient temperature and washed. The evolution of the size of the embryos during the storage period is observed.

The following results are obtained: Size of the embryos (μm)

| | Storage time | |
|---|---|---|
| | 0 | 1 month |
| Advanced heart embryos | | |
| Hypoxia in oil | 1100 | 1300 |
| Control | 1100 | 2470 |
| Torpedo embryos | | |
| Hypoxia in oil | 1320 | 1750 |
| Control | 1320 | 2790 |

As in Example 4, it can be seen that the embryos under hypoxia in oil grow more slowly than the control embryos.

The embryos are cultured for 10 days on a Murashige and Skoog semi-solid medium, after which the viability level is determined.

The following results are obtained:

| | Viability level (%) |
|---|---|
| Advanced heart embryos | |
| Hypoxia in oil | 76 |
| Control | 84 |
| Torpedo embryos | |
| Hypoxia in oil | 71 |
| Control | 95 |

We claim:

1. A process for preserving plant embryos comprising coating a plant embryo isolated from culture medium with an amount of oil sufficient for causing hypoxia, cooling the oil-coated embryo to a temperature above a cold sensitivity threshold of the embryo, and storing the oil-coated embryo at a temperature above the cold sensitivity threshold of the embryo.

2. A process according to claim 1 wherein the oil-coated embryo is stored at a temperature which is 1° C. to 10° C. above the cold sensitivity threshold of the embryo.

3. A process according to claim 1 wherein the embryo is a somatic embryo.

4. A process according to claim 1 wherein the embryo is a zygotic embryo.

5. A process according to claim 1 wherein the embryo is a somatic carrot embryo, which is stored at a temperature of 2° C. to 8° C.

6. A process according to claim 1 wherein the embryo is a somatic coffee tree embryo, which is stored at a temperature of 12° C. to 20° C.

7. A process according to claim 1 wherein the oil is selected from the group of oils consisting of mineral oil, oil of vegetable origin, and synthetic oil.

8. A process according to claim 1 wherein the oil is a liquid paraffin oil.

9. A process according to claim 1 wherein the embryo is stored in darkness.

10. A process according to claim 1 wherein the embryo is obtained from an embryo culture, and further comprising, before coating the embryo with oil, washing the embryo with a liquid culture medium and withdrawing residual culture medium from the embryo.

11. A process according to claim 10 wherein the liquid culture medium is free of growth hormones.

12. A process according to claim 1 further comprising encapsulating the oil-coated embryo with a polymer.

13. A process according to claim 12 further comprising coating the polymer-encapsulated oil-coated embryo with a water-soluble resin.

14. An oil-coated plant embryo composition obtained by coating a plant embryo isolated from culture medium with an amount of oil sufficient for causing hypoxia, cooling the oil-coated embryo to a temperature above a cold sensitivity threshold of the embryo, and storing the oil-coated embryo at a temperature above the cold sensitivity threshold of the embryo.

15. An oil-coated plant embryo composition obtained by coating a plant embryo isolated from culture medium with an amount of oil sufficient for causing hypoxia, cooling the oil-coated embryo to a temperature above a cold sensitivity threshold of the embryo, storing the oil-coated embryo at a temperature above the cold sensitivity threshold of the embryo, and encapsulating the oil-coated embryo with a polymer.

16. An oil-coated plant embryo composition obtained by coating a plant embryo isolated from culture medium with an amount of oil sufficient for causing hypoxia, cooling the oil-coated embryo to a temperature above a cold sensitivity threshold of the embryo, storing the oil-coated embryo at a temperature above the cold sensitivity threshold of the embryo, encapsulating the oil-coated embryo with a polymer, and coating the polymer-encapsulated oil-coated embryo with a water-soluble resin.

17. A plant embryo coated with an amount of oil sufficient to cause hypoxia.

18. An oil-coated plant embryo according to claim 17 encapsulated by a polymer.

19. A polymer-encapsulated oil-coated plant embryo according to claim 18 further coated with a water-soluble resin.

* * * * *

UNITED STATES PATENT AND TRADEMARK OFFICE
CERTIFICATE OF CORRECTION

PATENT NO. : 5,138,793
DATED : August 18, 1992
INVENTOR(S) : FLORIN, et al.

It is certified that error appears in the above-identified patent and that said Letters Patent is hereby corrected as shown below:

On the title page, under the heading "OTHER PUBLICATIONS", the title of the Augereau, et al., publication should be --Long Term Storage of Callus Cultures at Low Temperatures or Under Mineral Oil--.

Column 1, line 24, after "reristems" insert a comma.

Column 1, line 25, after "root" insert a comma.

Column 1, line 30, "in vitro" should be italicized.

Column 1, line 45, after "-20°C." insert --to--.

Signed and Sealed this

Twenty-first Day of September, 1993

Attest:

BRUCE LEHMAN

*Attesting Officer*  *Commissioner of Patents and Trademarks*